United States Patent
Fortin

(10) Patent No.: US 8,365,752 B1
(45) Date of Patent: Feb. 5, 2013

(54) OUTDOOR TANNING ENCLOSURE

(76) Inventor: Sharolyn Fortin, Sanbornton, NH (US)

( * ) Notice: Subject to any disclaimer, the term of this patent is extended or adjusted under 35 U.S.C. 154(b) by 218 days.

(21) Appl. No.: 12/459,223

(22) Filed: Jun. 29, 2009

Related U.S. Application Data

(60) Provisional application No. 61/133,238, filed on Jun. 27, 2008.

(51) Int. Cl.
*E04H 15/58* (2006.01)
*A61N 5/06* (2006.01)

(52) U.S. Cl. .......... 135/148; 135/91; 135/115; 135/117; 607/88; 607/95

(58) Field of Classification Search .......... 135/87, 135/115–117, 119, 121, 137, 148, 157, 902, 135/907, 913; 220/9.1–9.5; 446/119, 122; 607/81, 88, 95; 5/417–420, 656–657
See application file for complete search history.

(56) References Cited

U.S. PATENT DOCUMENTS

| | | | | |
|---|---|---|---|---|
| 1,650,323 A * | 11/1927 | Byars | | 135/120.1 |
| 1,669,484 A | 5/1928 | Mowry | | |
| 1,778,815 A | 10/1930 | Scrivner et al. | | |
| 2,168,913 A * | 8/1939 | Middleton | | 135/157 |
| 2,511,452 A * | 6/1950 | Anderson et al. | | 135/157 |
| 3,050,067 A * | 8/1962 | Trafton | | 607/95 |
| 3,326,225 A * | 6/1967 | Banks | | 135/117 |
| 3,391,409 A * | 7/1968 | Gatley | | 4/602 |
| 3,498,587 A | 3/1970 | Friedberg | | |
| 3,800,814 A * | 4/1974 | Hibbert | | 135/93 |
| D313,847 S | 1/1991 | Higgins | | |
| 5,010,909 A * | 4/1991 | Cleveland | | 135/125 |
| 5,072,828 A * | 12/1991 | Irvine | | 220/4.33 |
| 5,085,212 A | 2/1992 | DeCosta | | |
| 5,226,689 A * | 7/1993 | Roe et al. | | 296/159 |
| 5,387,230 A | 2/1995 | Minor | | |
| 5,446,580 A | 8/1995 | Collins | | |
| 5,518,798 A | 5/1996 | Riedel | | |
| 5,733,314 A | 3/1998 | Perrino | | |
| 5,837,000 A | 11/1998 | Boudreau | | |
| 6,098,218 A * | 8/2000 | Ventura | | 5/113 |
| 6,206,079 B1 * | 3/2001 | Selgrad | | 160/351 |
| 6,585,751 B1 | 7/2003 | Silverman | | |
| 7,044,083 B2 * | 5/2006 | Farmer et al. | | 119/474 |
| 7,216,381 B1 | 5/2007 | Setzer | | |

* cited by examiner

*Primary Examiner* — Winnie Yip
(74) *Attorney, Agent, or Firm* — Montgomery Patent & Design LLC; Robert C. Montgomery

(57) ABSTRACT

An enclosure intended to provide privacy and protection when tanning outdoors is herein disclosed, utilizing a lightweight frame. All sides are covered with a screen material and feature opaque panels that can be rolled up to allow for air flow or let down to provide privacy. The screen material provides for protection against insects as well. The roof of the enclosure is made of clear plastic through which the transmission of ultraviolet rays is still possible, thus allowing for tanning. Entrance into the enclosure is provided through a zippered opening at each end. The enclosure can be easily disassembled for ease of transportation or storage when not in use.

16 Claims, 11 Drawing Sheets

OUTDOOR TANNING ENCLOSURE

RELATED APPLICATIONS

The present invention was first described in and claims the benefit of U.S. Provisional Patent No. 61/133,238 filed Jun. 27, 2008, the entire disclosures of which are incorporated herein by reference.

FIELD OF THE INVENTION

The present invention relates generally to tanning enclosures and, more particularly, to an outdoor tanning enclosure designed to provide privacy and protection to a sunbather.

BACKGROUND OF THE INVENTION

Much time, effort and money are spent outdoors, in tanning booths, and on special lotions and oils to generate the ideal tan. While tanning salons and self tanning lotions have become increasingly popular, many people still choose to sunbathe at the beach, lake, park, yard, or similar outdoor location. The biggest disadvantage to sunbathing in these locations is the lack of privacy. People just do not feel comfortable lying naked or nearly naked in the presence of others in order to obtain a tan. Nude sunbathing is a violation of law in most public locations. Additionally, when tanning outdoors the sunbather is routinely bothered and bitten by insects. These factors make it difficult to enjoy the rest and relaxation commonly associated with sunbathing and can make obtaining a full body tan with no tan lines nearly impossible.

The use of tanning screens for privacy is well known, more particularly, attempts to provide privacy tanning enclosures utilizing expected configurations and designs are as well known. These attempts can be seen by reference to several U.S. patent numbers, including U.S. Pat. No. 1,669,484; U.S. Pat. No. 1,778,815; U.S. Pat. No. 3,498,587; U.S. Pat. No. 5,733,314; U.S. Pat. No. 5,837,000; U.S. Pat. No. 5,085,212; U.S. Pat. No. 5,387,230; U.S. Pat. No. 5,446,580; U.S. Pat. No. 6,585,751; and U.S. Pat. No. 7,216,381.

Additionally, ornamental designs for sun bathing tubs and the like exist, particularly, U.S. Pat. number D 313,847. However, none of these designs are similar to the present invention.

While these attempts fulfill their respective, particular objectives, each of these solutions suffers from one (1) or more common deficiency including, a lack of versatility and portability, bulky construction, restrictions to the number of users at a given time, or complexity in the set up and break down of the enclosure. Accordingly, there is a need for a means by which anyone can sunbathe outdoors and have a high degree of privacy and protection anytime without the disadvantages mentioned above. The development of the present invention substantially departs from the conventional solutions and in doing so fulfills this need.

SUMMARY OF THE INVENTION

In view of the foregoing references, the inventor recognized the aforementioned inherent problems and observed that there is a need for a tanning enclosure that provides privacy or protection to a sunbather comprising a lightweight frame having mesh-like side panels that allows airflow, removable canvas-like opaque side panels, a transparent top panel which enables the transmission of ultraviolet rays, internal storage pockets, a carrying case and thus, the object of the present invention is to solve the aforementioned disadvantages and provide for this need.

To achieve the above objectives, it is an object of the present invention to provide a tanning tent that provides a protected and private enclosure for use in various outdoor public locations comprising a durable and reliable construction that is easy and convenient to transport, set up and disassemble.

Yet still another object of the present invention is to provide an apparatus generally comprising an enclosure, a collapsible frame, a plurality of pockets, a plurality of zippers, and a storage enclosure. The collapsible frame is fabricated of lightweight tubing capable of withstanding typical outdoor environmental effects over a long period of time. The enclosure is fabricated of durable material.

Yet still another object of the present apparatus is to provide a cover enclosure comprising a first side panel, a second side panel, a pair of end panels, a bottom panel, and a top panel.

Yet still another object of the present apparatus is to provide a frame comprising a plurality of connection pieces that provide a supporting means to the cover enclosure in an extended orientation. The frame comprises of four (4) "U"-shaped connection pieces, four (4) end pieces, and two (2) longitudinal pieces.

Yet still another object of the present apparatus is to provide side panels and end panels comprising two (2) layers: an outer canvas-like layer and an inner mesh-like layer. The canvas-like material resists environmental conditions, thereby allowing a user to utilize the apparatus in cool conditions. The mesh-like material is utilized by rolling up the outer canvas-like layer and upwardly securing it with a sewn-in tie, thus exposing the mesh-like layer that permits airflow through the interior of the apparatus and provides the user to benefit from a summer breeze.

Yet still another object of the present apparatus is to provide two (2) end panels comprising an entrance and exit aperture which permits access to an interior sunbathing space within the apparatus.

Yet still another object of the present apparatus is to provide an embodiment of the apparatus comprising a top panel that filters a specific wavelength or a combination of wavelengths, of sunlight passing through, thereby offering a degree of protection to the user within.

Yet still another object of the present apparatus is to provide an apparatus that enables a plurality of users to sunbathe, relax, or perform other activities in a manner which provides privacy from onlookers, insects, or other annoyances.

Yet still another object of the present apparatus is to provide the frame that may be set up in an upright and extended orientation such that at least one (1) user may be enclosed within in a lying or seated position.

Yet still another object of the present apparatus is to provide the frame and a cover enclosure that are simply disassembled and collapsible such that the apparatus is easily transportable from location to location and that requires minimum space when not in use.

Yet still another object of the present apparatus is to provide a storage enclosure that enables the disassembled and collapsed frame and cover enclosure to be packed and carried.

Yet still another object of the present apparatus is to provide a method of utilizing the device that provides sunbathers a means to obtain a rich, even tan outdoors in total privacy.

Further objects and advantages of the present apparatus will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
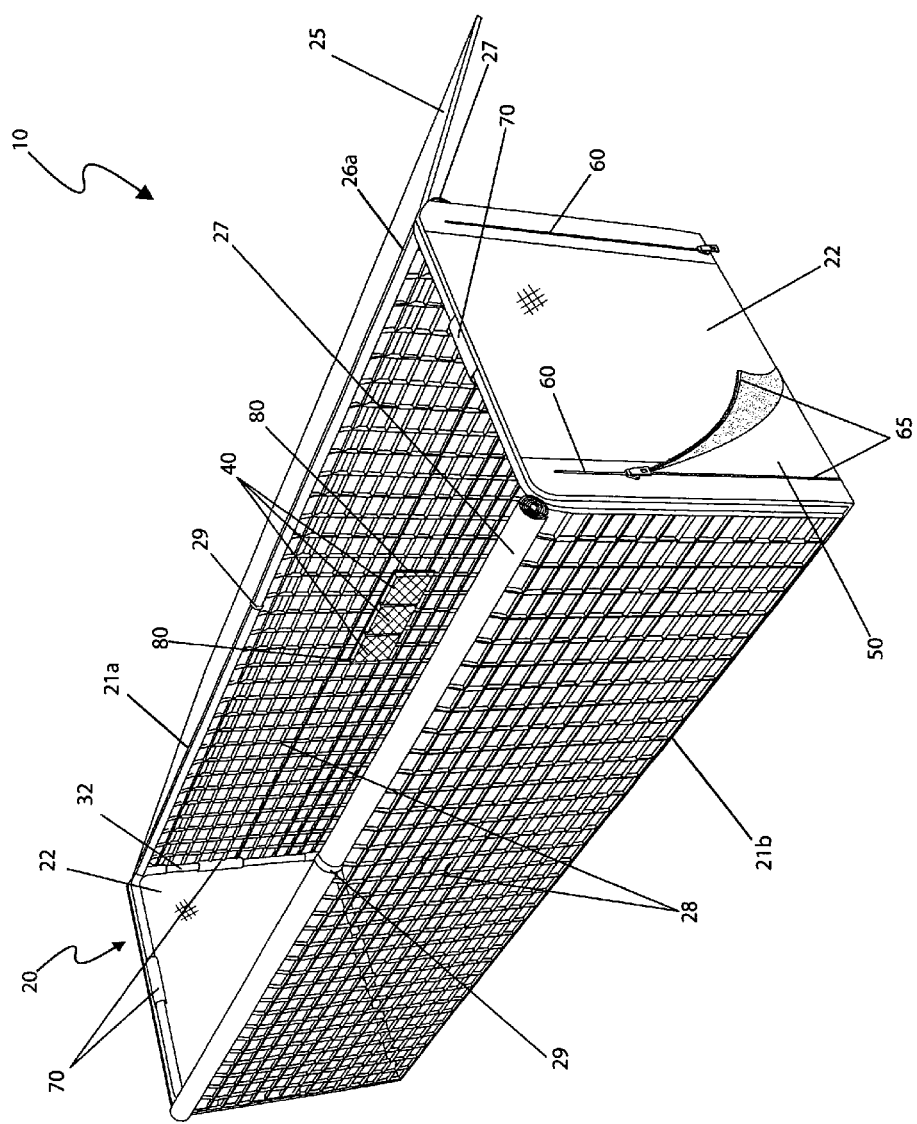
FIG. 1 is a perspective view of a tanning tent 10 depicting an extended orientation, according to the preferred embodiment of the present invention.

DESCRIPTIVE KEY 10 tanning tent
20 enclosure
21a first side panel
21b second side panel
21c longitudinal pocket
22 end panel
23 bottom panel
25 top panel
26a connection material
26b connection fastener
26c grommet
27 canvas-like material
28 mesh-like material
29 tie frame
31 longitudinal connection piece
32 end connection piece
33 "U"-shaped connection piece
34 aperture
35 receiving aperture
40 pocket
50 entrance/exit aperture
60 zipper
65 zipper track
70 strap
80 sewing technique
90 storage enclosure
92 body
94 opening
96 handle

DETAILED DESCRIPTION OF THE PREFERRED EMBODIMENT

The best mode for carrying out the invention is presented in terms of its preferred embodiment, herein depicted within FIGS. 1 through 11. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a tanning tent (herein described as the "apparatus") 10 that which encloses a user in a private setting for tanning outdoors under safe conditions against ultraviolet (UV) rays. The apparatus 10 comprises an enclosure 20, a collapsible frame 30, a plurality of pockets 40, a plurality of zippers 60, and a storage enclosure 90. The collapsible frame 30 is fabricated of plastic or metallic tubing made in an extrusion process. The materials are capable of withstanding the typical outdoor environmental effects such as, but not limited to, heat, rain, snow, and freezing conditions especially over a long period of time. The enclosure 20 is preferably fabricated of nylon or similar material commonly used in the fabrication of tents. The apparatus 10 is placed on the ground, preferably outdoors, by users who desire to sunbathe, relax, and/or other activities in which a user may do with some degree of privacy. The frame 30 may be set up on the ground to stand upright in an extended orientation such that at least one (1) user may be positioned therein. The frame 30 may be set on typical ground settings, i.e. grass, dirt, sand, etc; alternatively the frame 30 may be set on a deck floor, patio, concrete pad, etc.

Referring now to FIG. 1, a perspective view of the apparatus 10 depicting an extending orientation is herein disclosed according to the preferred embodiment of the present invention. The apparatus 10 is introduced in a plurality of dimensions to accommodate one (1) person of various sizes and/or may allow more than one (1) person at a time. The apparatus 10 may be dimensioned to allow the user to stand therewithin or alternatively be at a height which would only allow the user to lay down on a lounge chair or the like. The apparatus 10 comprises an enclosure system 20 which comprises a nylon and/or canvas-like material 27 which could resist environmental conditions and provide an amount of protection from harmful ultraviolet rays. The enclosure 20 also comprises a mesh-like material 28 which would allow ultraviolet rays to pass therethrough as well as airflow.

Figure 2:
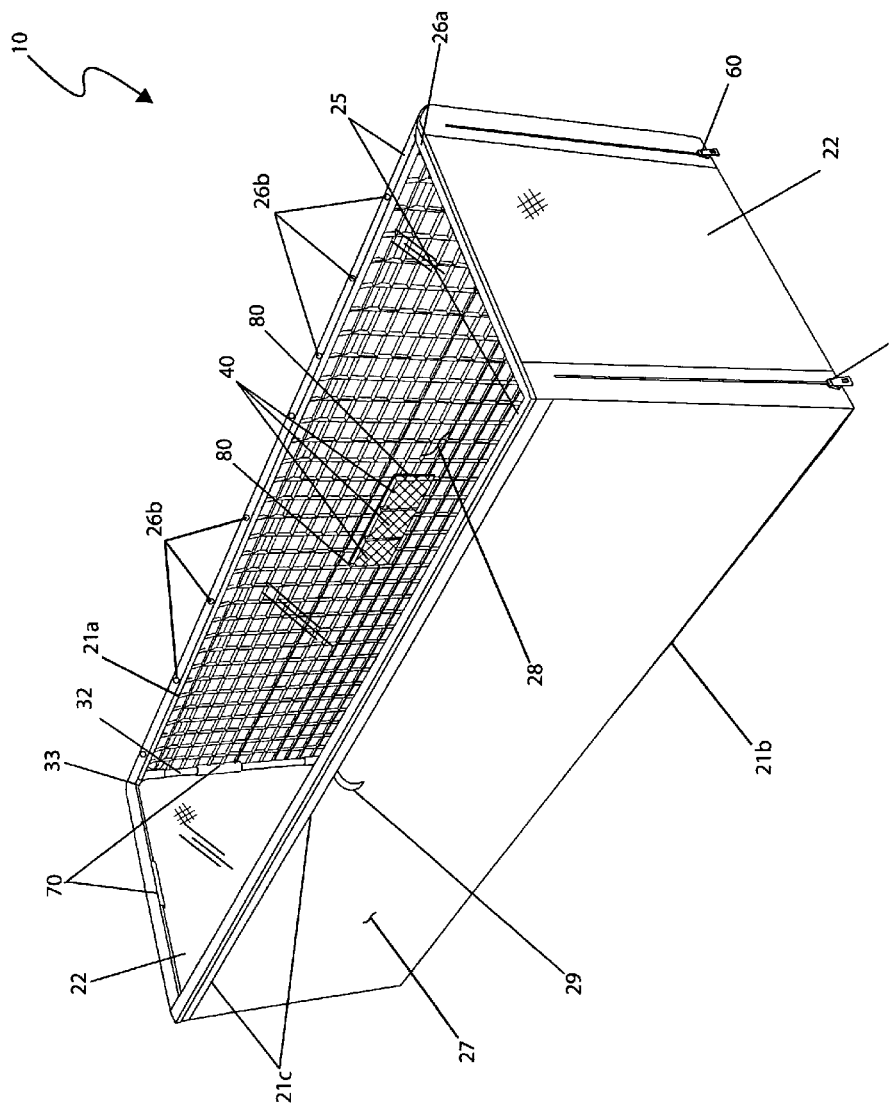
FIG. 2 is a perspective view of the tanning tent 10 depicting an in-use extended orientation, according to the preferred embodiment of the present invention.
Figure 3:
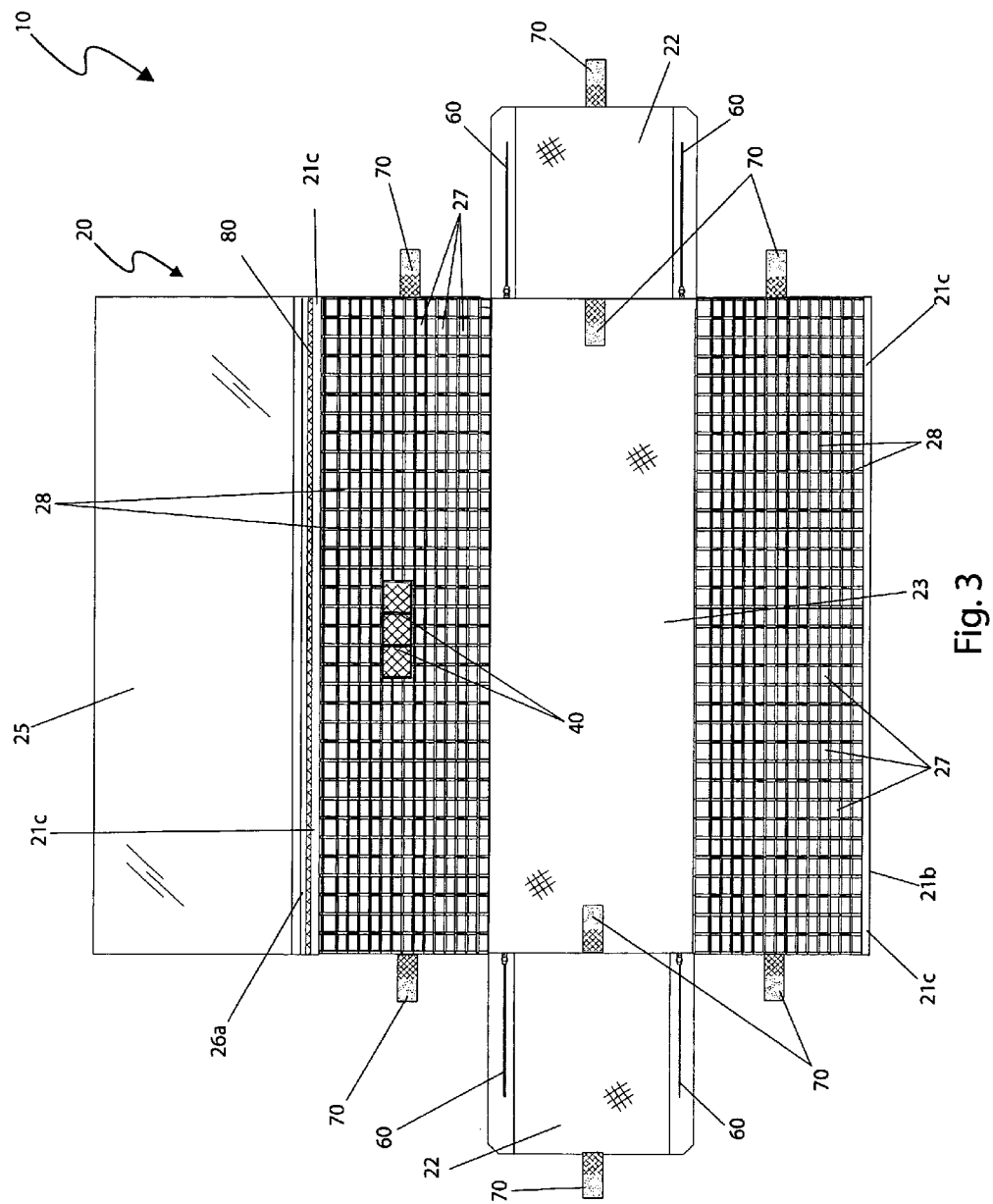
FIG. 3 is a top view of the tanning tent 10 depicting a collapsed state, according to the preferred embodiment of the present invention.
Figure 4:
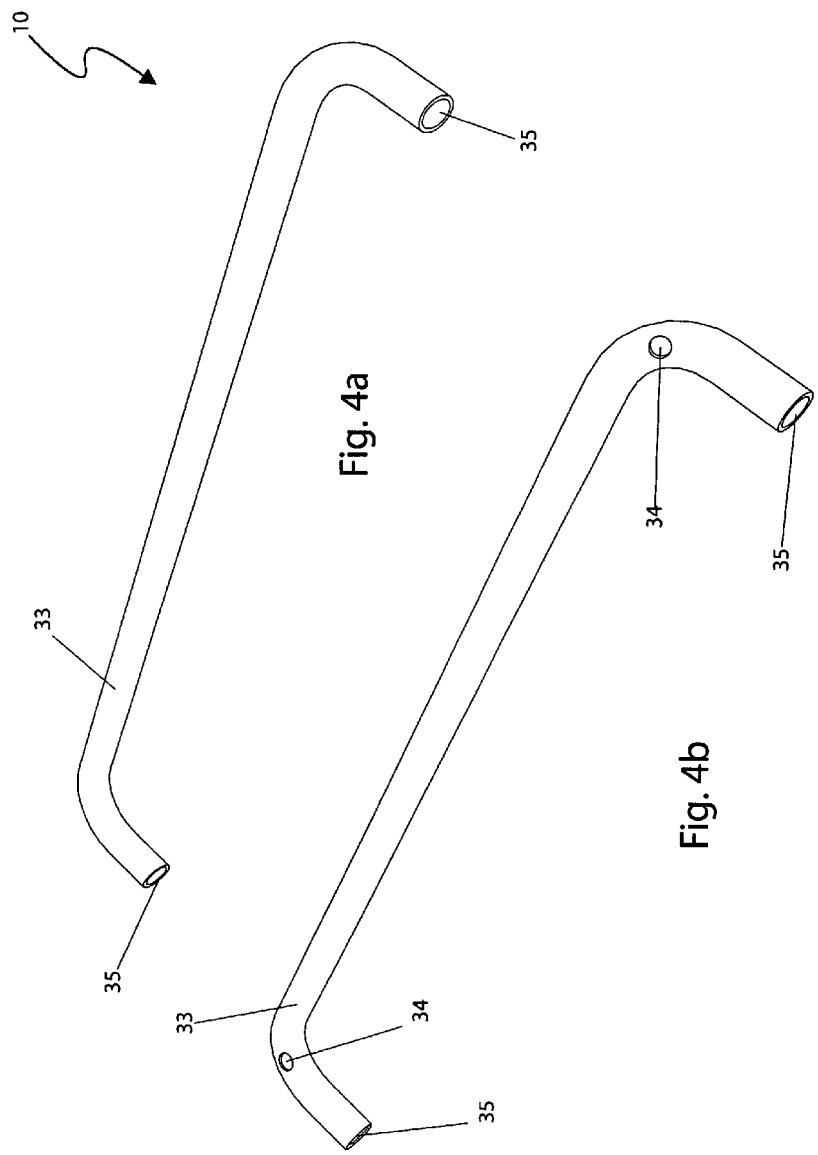
FIG. 4a is a perspective view of a "U"-shaped connection piece 33 utilized thereon a frame 30, according to the preferred embodiment of the present invention.
FIG. 4b is an opposing perspective view of the "U"-shaped connection piece 33 utilized thereon the frame 30, according to the preferred embodiment of the present invention.
Figure 5:
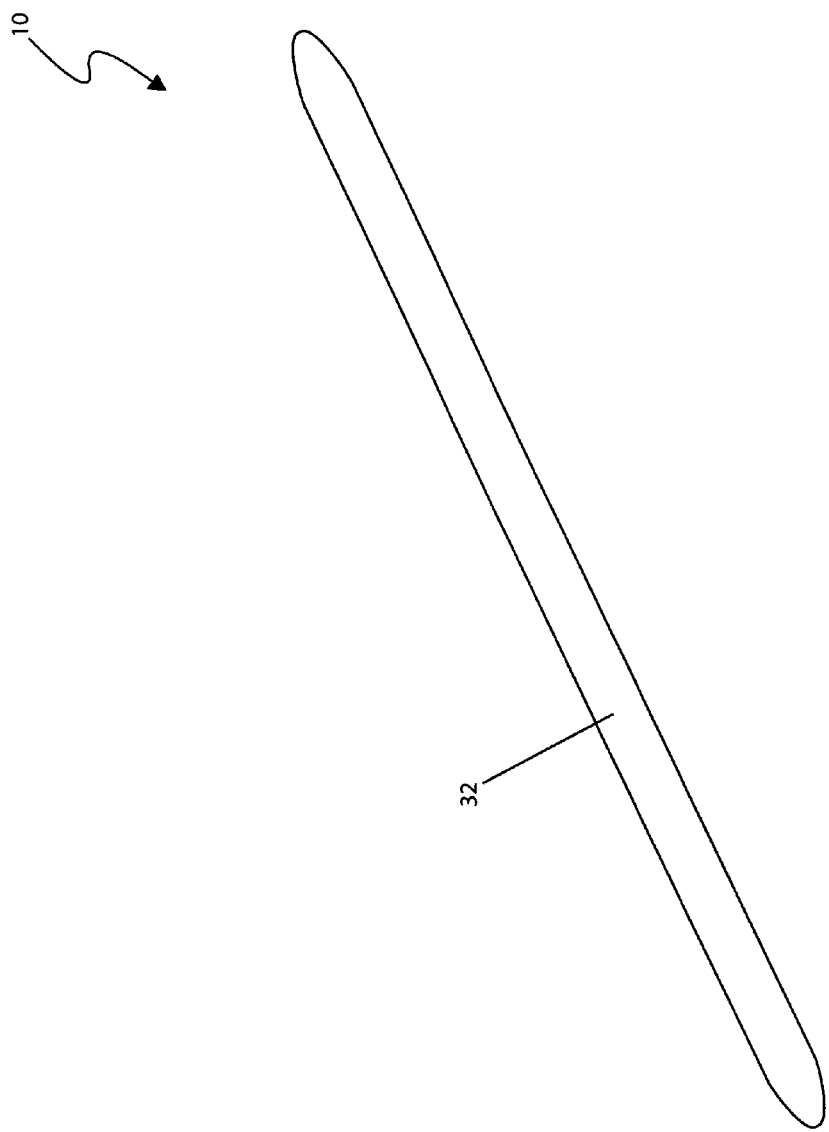
FIG. 5 is a perspective view of an end connection piece 32 utilized thereon the frame 30, according to the preferred embodiment of the present invention.
Figure 6:
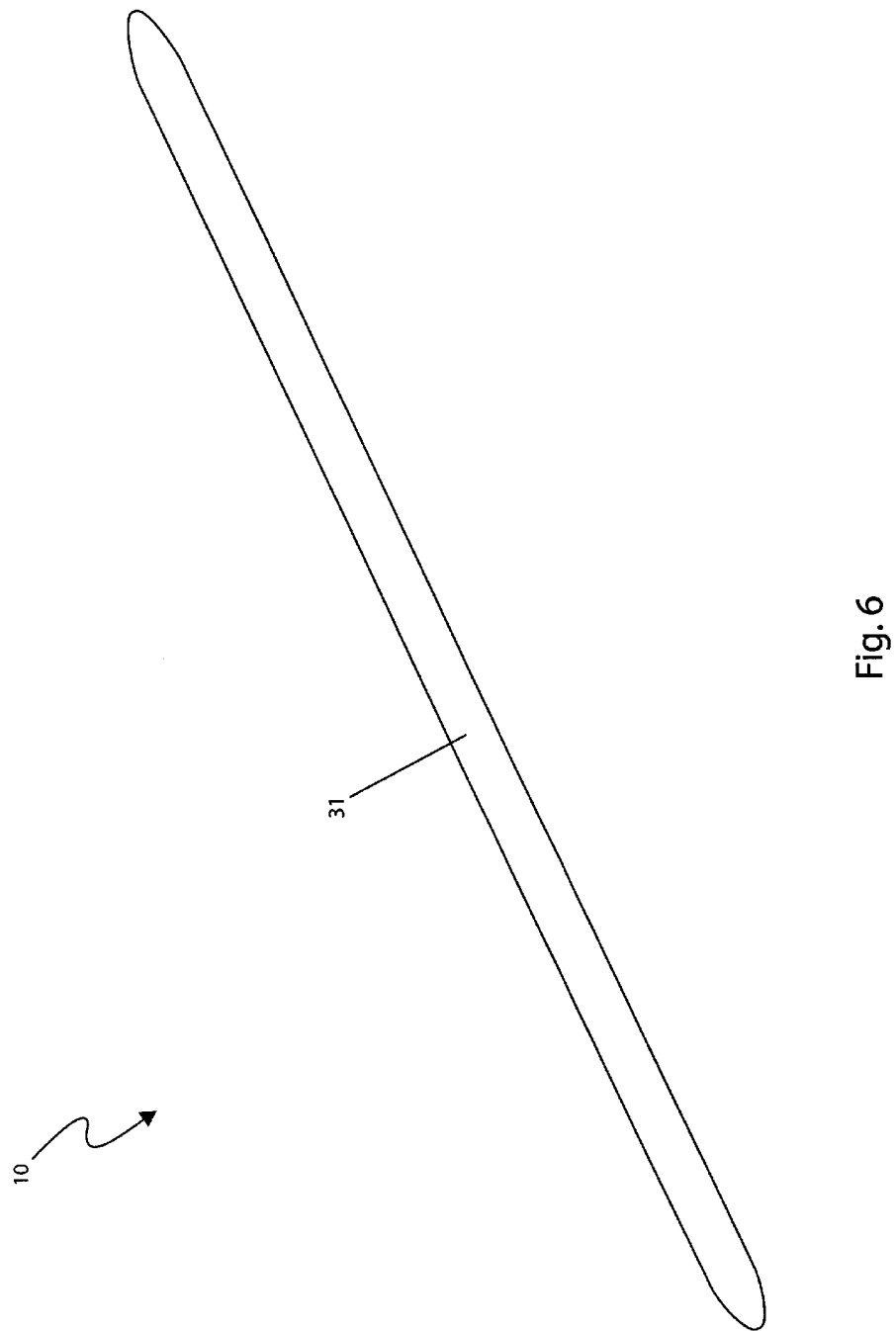
FIG. 6 is a perspective view of a longitudinal connection piece 31 utilized thereon the frame 30, according to the preferred embodiment of the present invention.
Figure 7:
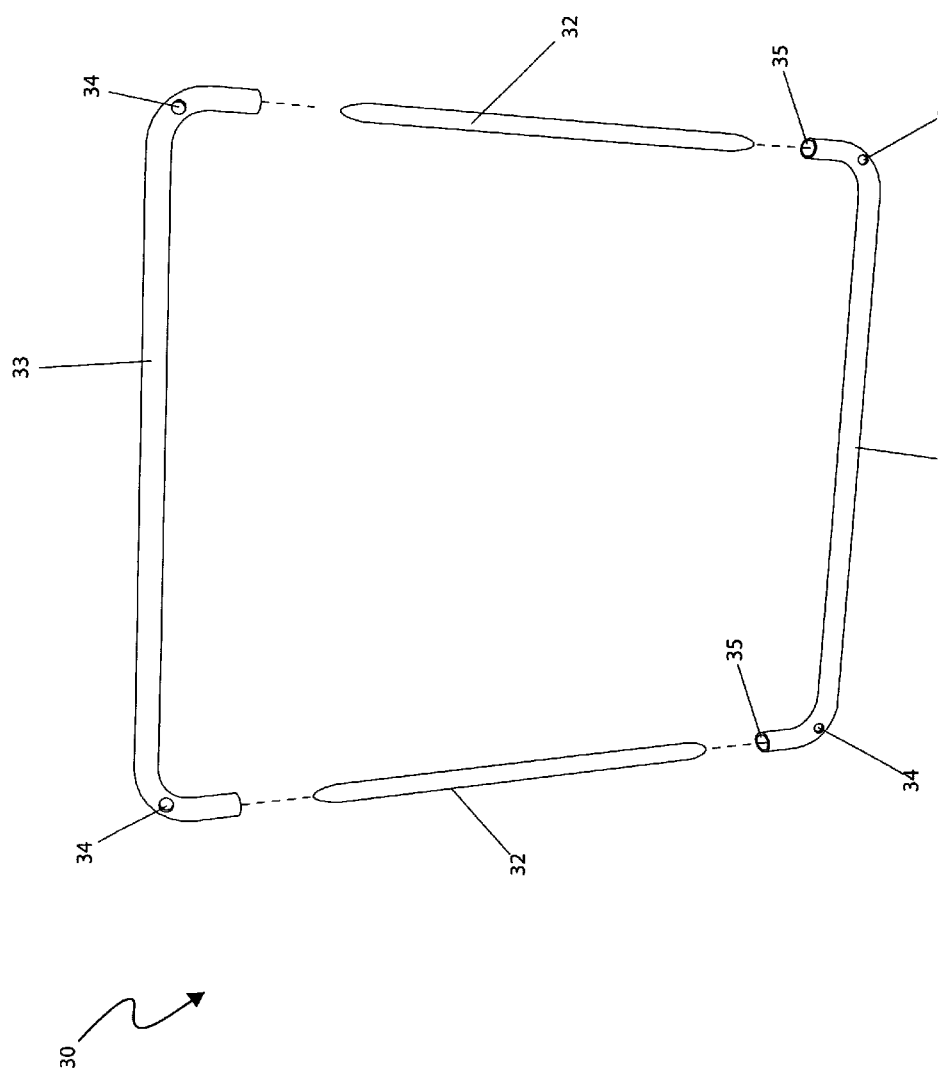
FIG. 7 is an exploded perspective view of the frame 30, according to the preferred embodiment of the present invention.
Figure 8:
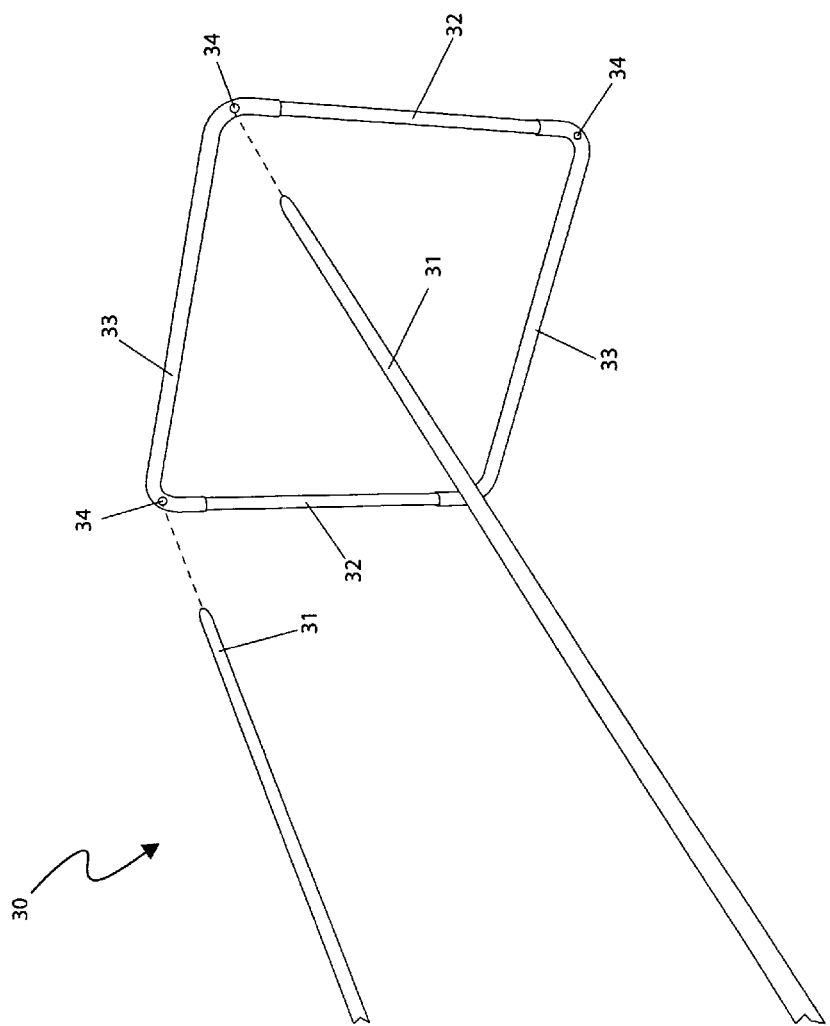
FIG. 8 is a partially exploded perspective view of the frame 30, according to the preferred embodiment of the present invention.

Referring now to FIG. 2, a perspective view of the apparatus 10 depicting an in-use extended orientation and FIG. 3, a top view of the apparatus 10 depicting a collapsed state, are herein disclosed according to the preferred embodiment of the present invention. The abovementioned enclosure 20 comprises a first side panel 21a, a second side panel 21b, a pair of end panels 22, a bottom panel 23, and a top panel 25. Two (2) side panels 21a, 21b are stitched, adhered, integrated, or otherwise attached thereto the longitudinal sides of the bottom panel 23 in a parallel arrangement with each other. The bottom panel 23 is stitched, adhered, integrated, or otherwise attached thereto along the entire periphery to two (2) previously mentioned side panels 21a, 21b and two (2) end panels 22. Each end panel 22 is stitched, adhered, integrated, or otherwise attached thereto the lateral sides of the bottom panel 23 in a parallel arrangement with each other and a perpendicular arrangement with the previously mentioned side panels 21a, 21b. The width of the side panels 21a, 21b, end panels 22, bottom panel 23 and top panel 25 are to be similar dimensions. The size of the side panels 21a, 21b are the same as the bottom panel 23 and top panel 25 and preferably, but not essentially, the lengths of said panels 21a, 21b, 23, 25 are a multiple of the end panels 22, for example the side panels 21a, 21b are twice as long as the end panels 22. In such a manner, the enclosure 20 may be collapsed inwardly and the side panels 21a, 21b, bottom panel 23, and top panel 25 may be folded in half laterally thereby matching the dimensions of the end panels 22. Such compaction methods would allow easy storage.

The side panels 21a, 21b and the end panels 22 are introduced in two (2) layers: an outer nylon and/or canvas-like layer 27 (as shown in FIG. 2) and a screen or mesh-like material layer 28 (as shown in FIG. 1). The nylon and/or canvas-like material 27 would resist environmental conditions and provide protection from a chilling breeze or the like, thereby allowing a user to use the apparatus 10 in cool conditions. Integrally attached thereto the underside surface of each side panel 21a, 21b and end panel 22 is a screen or mesh-like material 28 which could be used instead of the outer canvas-like material layer 27, thereby allowing a user to roll up the outer canvas-like material layer 27 and securing upwardly with a sewn-in tie 29 and exposing the mesh-like material 28, as depicted in FIG. 2. The tie 29 is located at an upper intermediate position thereon an outer and inner portion of the canvas-like material 27 and fabricated from a fabric similar to said canvas-like material 27. The mesh-like material 28 would allow the user to benefit from a summer breeze thereby permitting airflow therethrough the interior of the apparatus 10. The porous nature of both layers 27, 28 permits ultraviolet light to pass therethrough for facilitating tanning of a user while the user is within the apparatus 10. Further, each layer 27, 28 would give obstructed views to the interior thereof thereby providing privacy to the user.

The top panel 25 is fabricated of a high visibility clear plastic designed for permitting light to pass through to the user when the user is positioned in the interior space of the apparatus 10. The top panel 25 may also be tinted a certain degree to offer a certain amount of protection from harmful ultraviolet rays. Said top panel 25 is attached to distal longitudinal portion of the first side panel 21a therewith a connection material 26a and conventional sewing techniques 80 (also see FIGS. 9 and 10). A hinging means is created via the connection material 26a as a result of attaching the top panel 25 to the first side panel 21a via said connection material 26a. Alternatively, the top panel 25 may be designed to filter a specific wavelength or a combination of wavelengths of sunlight passing therethrough thereby offering a certain degree of protection thereto the user therewithin.

The inside surface of the first side panel 21a comprises pockets 40, pouches, receptacles, holders, or the like mounted, integrated, adhered, or otherwise integrally disposed thereon protruding outwardly from surface, conveniently located for easy and quick access, to store various items so as to provide easy and convenient access therein. The pockets 40, pouches, receptacles, holders, or the like may comprise a flap that can be openly closed with a fastening mechanism such as, but not limited to, zippers, hook-and-loop fasteners, buttons, snaps, or the like to fully envelope the items residing therein. The size of said pockets 40, pouches, receptacles, holders or the like are introduced in a plurality of dimensions suitable for receiving and holding one (1) or more articles of various sizes and weights and are preferably attached to the first side panel 21a therewith sewing techniques 80.

Integrally positioned on each end panel 22 is an entrance/exit aperture 50 (see FIG. 1) which would permit access to the interior space therewithin the apparatus 10. The entrance/exit aperture 50 may be sized in a plurality of dimensions to accommodate a user of various size and weight or a plurality of users to pass therethrough simultaneously. The aperture 50 may be selectively closed and opened via a pair of fastening mechanisms such as a zipper 60 for example. The zippers 60 would travel therealong a zipper track 65 (shown in FIG. 1) thereby engaging or disengaging zipper teeth integrally disposed therealong said zipper track 65. The engagement or disengagement of the zipper teeth would ultimately depend on the zippers 60 and the motion of the zippers 60 thereof. It will be appreciated that alternate methods of closing and/or opening the entrance/exit aperture 50 may be introduced without limiting the functions of the apparatus 10.

Referring now to FIGS. 4a through 8, various views of the frame system 30, are herein disclosed according to the preferred embodiment of the present invention. The tubular frame system 30, comprises a plurality of connection pieces 31, 32, 33 utilized as supporting means, supports the enclosure 20 in the extended orientation. The frame 30 comprises of four (4) "U"-shaped connection pieces 33, four (4) end pieces 32, and two (2) longitudinal pieces 31. All of the connection pieces 31, 32, 33 are arranged in a hollow cylindrical fashion much like a tube so that the frame 30 may be lightweight, yet sturdy. Each end piece 32 and longitudinal piece 31 comprises a distal end and a proximal end, which are similar in shape and size in comparison with each other, and are tapered inwardly such to create a smaller diameter thereof. The tapered ends taper inwardly to a certain diameter which spans a certain length, i.e. three (3) inches for example, to be removably receivable therein enlarged receiving apertures 35 positioned at the proximal and distal ends of the "U"-shaped connection piece 33. Each "U"-shaped connection piece 33 comprises a distal end and a proximal end, which are similar in shape and size in comparison with each other, taper outwardly such to create a larger diameter thereof. The distal and proximal end each comprise two (2) receiving apertures 35 which are sized to removably receive the smaller tapered ends of the end piece 32.

At each end of the apparatus 10, the frame 30 is shaped much like a square with the two (2) "U"-shaped pieces 33 arranged in a vertical arrangement parallel thereto each other and two (2) end pieces 32 arranged in a horizontal arrangement parallel thereto each other. The distal ends of each end piece 32 are inserted therein the enlarged receiving apertures 35 positioned at the distal and proximal ends of one (1) "U"-shaped member 33, and the proximal ends of each end piece 32 are inserted therein the enlarged receiving apertures 35 positioned at the distal and proximal ends of the opposing "U"-shaped member 33. The smaller ends of the end pieces 32 are inserted therein the enlarged receiving apertures 35 of the "U"-shaped members in a manner in which the outside walls of the small tapered ends of the end pieces 32 abut thereagainst the inside walls of the enlarged receiving apertures 35. This arrangement produces an end frame portion that is placed at each end of the apparatus 10. The end frame portions are positioned in a parallel arrangement therewith one (1) another and connected therewith one (1) another utilizing longitudinal connection pieces 31. The "U"-shaped members 32 comprise an aperture 34 perpendicular therewith the central axis of the first enlarged hole in which the tapered ends of the end pieces 32 are removably received. Said apertures 34 receive the distal and proximal ends of each longitudinal piece 31. The smaller tapered ends of the longitudinal pieces 31 are inserted therein the second enlarged receiving holes of the "U"-shaped members 33 in a manner in which the outside walls of the small tapered ends of the longitudinal connection pieces 31 abut thereagainst the inside walls of the second enlarged receiving holes. This arrangement produces a rectangular box-like frame 30 that is designed to removably receive the enclosure 20. Prior to insertion of the longitudinal connection pieces 31 thereinto the apertures 34 said longitudinal connection pieces 31 are slidably inserted thereinto a longitudinal pocket portions 21c located thereon each distal end portions of the side panels 21a, 21b (see FIG. 9), thereby enabling said side panels 21a, 21b to be erected upwardly. Said longitudinal pockets 21c are created therewith conventional sewing techniques 80 and further enable each distal end of the longitudinal connection pieces 31 to be visible for placement thereinto the "U"-shaped connection piece 33.

On the inside surface of the side panels 21, top panel 25, and end panels 22 comprises straps 70 with hook-and-loop type fastening straps 70 (see FIGS. 1 through 3) to strategically encompass the circumference of the tubular connection pieces 31, 33 of the frame 30 thereby supporting and balancing the enclosure 20 onto the frame 30. The straps 70 are utilized to erect the enclosure 20 onto the collapsible frame 30. As illustrated in FIG. 3, the inside surfaces of the side panels 21a, 21b and end panels 22 comprises two (2) straps 70, positioned approximately central thereto the longitudinal length of each designated panel 21a, 21b, 22. The straps 70 are stitched, adhered, integrated, or otherwise attached thereto the designated ends of said panels 21a, 21b, 22, having another end for free movement such to allow said straps 70 to wrap around the frame connection pieces 31, 33. Each strap 70 comprises a hook fastener strip spanning across the partial length of said strap 70 and a loop fastener strip spanning across the remainder length of said strap 70. The hook-and-loop fastener assembly is sewn, adhered, integrated, or otherwise attached thereto the straps 70. The hook-and-loop fastener assembly comprises a hook fastener strip and a loop fastener strip which mate one (1) with the other.

Figure 9:
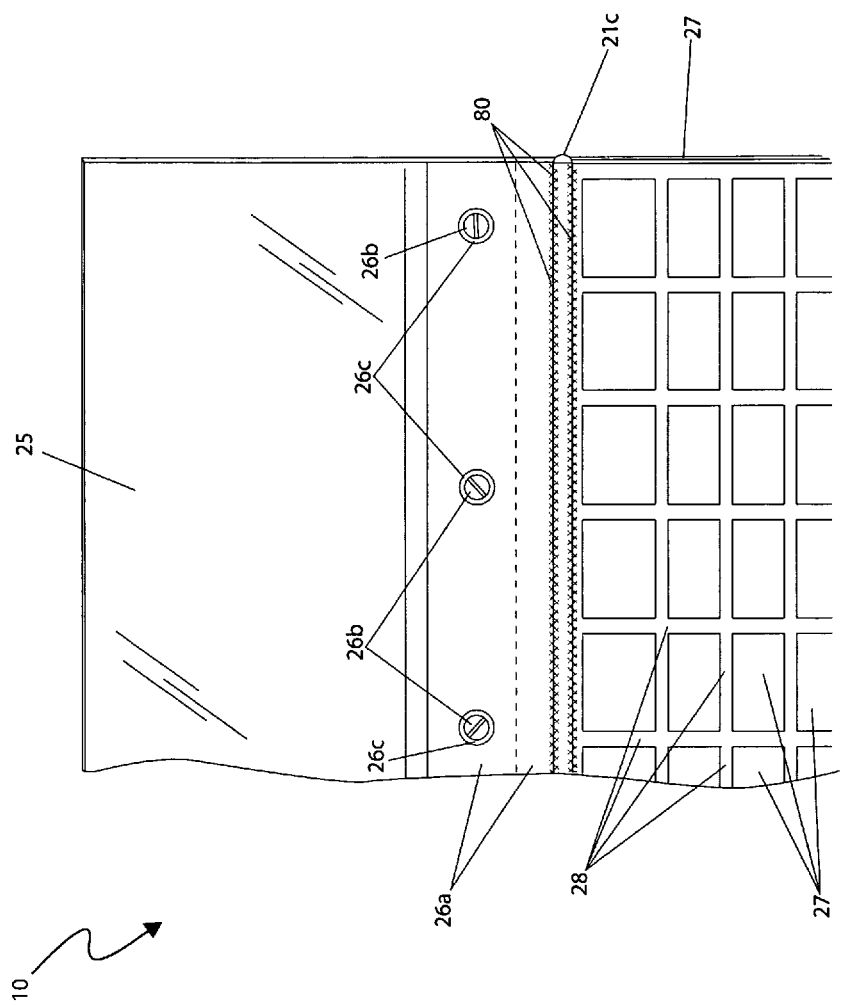
FIG. 9 is a close-up view of an attachment of a top panel 25 thereto a first side panel 21a, according to the preferred embodiment of the present invention.
Figure 10:
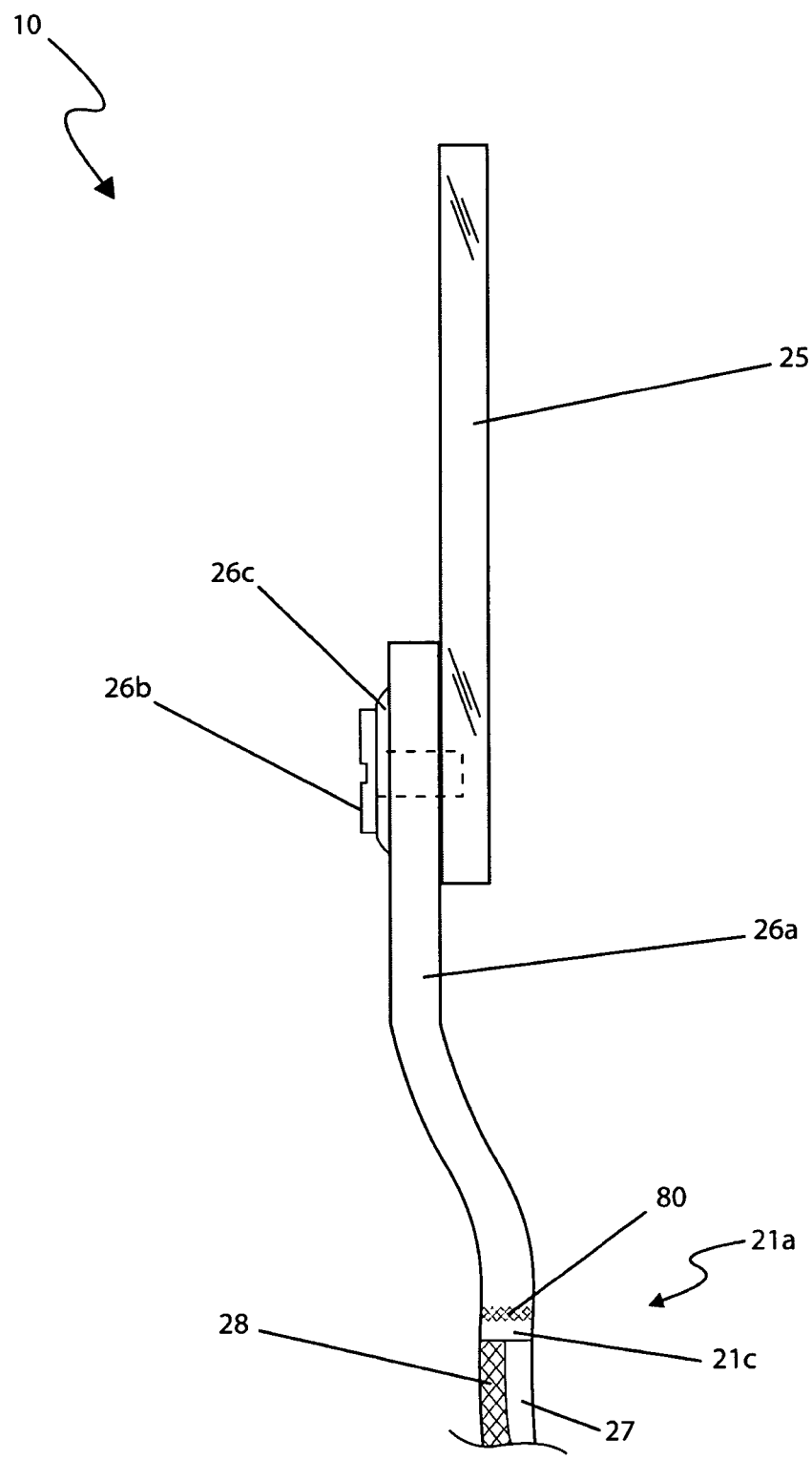
FIG. 10 is a side view of the attachment of the top panel 25 thereto the first side panel 21a, according to the preferred embodiment of the present invention; and, FIG. 11 is a perspective view of a storage enclosure 90, according to the preferred embodiment of the present invention.

Referring now to FIGS. 9 and 10, various views of the attachment of a top panel 25 thereto the first side panel 21a, are herein disclosed according to the preferred embodiment of the present invention. The apparatus 10 comprises a connection material 26a, thereby attaching the top panel 25 to the first side panel 21a and, thereby creating a hinging means to said top panel 25. The connection material 26a is secured thereto the distal longitudinal end portion of the first side panel 21a therewith conventional sewing techniques 80, yet other fastening means may be provided without limiting the functions of the apparatus 10. Said connection material 26a is also secured to the top panel 25 therewith a plurality of connection fasteners 26b and a plurality of grommets 26c. A distal portion of the connection material 26a comprises the plurality of conventional fabric grommets 26c in a horizontal fashion, thereby enabling insertion of corresponding connection fasteners 26b. The fasteners 26b are common screw-type fasteners, yet other fastening means may be utilized without limiting the functions of the apparatus 10. Said connection material 26a is preferably positioned superjacent to the top panel 25 and the connection fasteners 26b are inserted through an appropriate amount of grommets 26c and secured downwardly thereinto the top panel 25, thereby interconnecting the first side panel 21a thereto the top panel 25. The connection material 26a is fabricated from a material such as, but not limited to: canvas, plastic, or the like.

Figure 11:
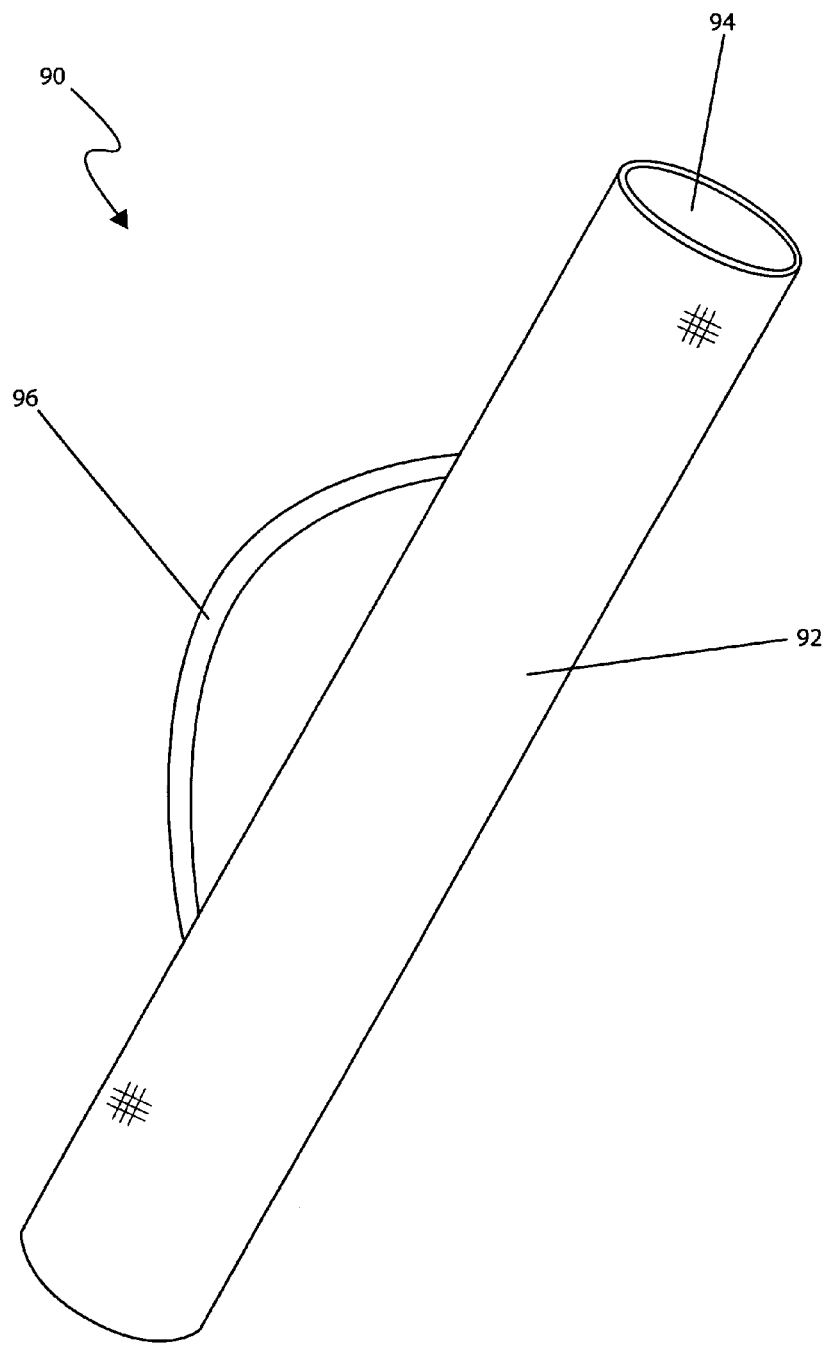

Referring now to FIG. 11, a perspective view of the storage enclosure 90, is herein disclosed according to the preferred embodiment of the present invention. The apparatus 10 preferably comprises a storage enclosure 90, thereby providing a housing means for the apparatus 10. Said storage enclosure 90 comprises a body 92, an opening 94, and a handle 96. The body 92 takes on a tubular form, yet other forms may be provided and is fabricated from materials such as, but not limited to: a durable fabric, a plastic, or the like in a variety of patterns or colors. Said body is an appropriate length and diameter thereto fit the apparatus 10. An upper distal portion of the body 92 comprises the opening 94, thereby providing an insertion means for the apparatus 10 thereinto an interior portion of the body 92. An intermediate portion of the body 92 comprises the handle 96, thereby providing a user therewith a gripping means thereto carry the apparatus 10 within the storage enclosure 90. Said handle 96 comprises an arcuate shape and is preferably fabricated from a material similar thereto the body 92.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIGS. 1 through 11.

The method of utilizing the apparatus 10 may be achieved by performing the following steps: acquiring the apparatus 10; removing from the storage enclosure 90; uniting the connection pieces 32, 33 by positioning the small tapered ends of the end connection piece 32 therein the receiving apertures 35 thereon the "U"-shaped connection piece 33; inserting each longitudinal connection piece 31 through each longitudinal pocket 21c; inserting each tapered end of each longitudinal connection piece 31 thereinto the apertures 34 thereon the "U"-shaped connection piece 33 until the tubular frame 30 is complete; utilizing the straps 70 with hook-and-loop assembly to secure the enclosure 20 onto the frame 30; optionally rolling up one (1) or more canvas-like material 27 and securing thereto the frame 30 via the tie 29; opening the entrance/exit aperture 50 via a zipper 60, for example; entering therein the apparatus 10; hinging the top panel 25 via the connection material 26a thereon a top portion of the frame 30; placing suntan lotion, lotions, sun block, and/or other personal items therein the pockets 40, as desired; utilizing the apparatus 10 as desired for sun bathing, tanning, or the like in a private manner; and, collapsing the apparatus 10, thereby unfastening the straps 70, removing the longitudinal connection pieces 31 from the longitudinal pockets 21c, and disassembling the frame 30; rolling or folding the apparatus 10 for placement therein the storage enclosure 90; inserting the connection pieces 31, 32, 33 thereinto the storage enclosure 90;

utilizing the handle 96 thereto carry the apparatus 10 to a desired storage area; and, utilizing said apparatus 10 as necessary.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A tanning enclosure, comprising:
   a collapsible frame, comprising a plurality of interconnected pieces; and,
   a cover enclosure removably attachable thereto said collapsible frame, further comprising:
      a first side panel having a waterproof outer resilient layer and an inner mesh layer;
      a second side panel having a waterproof outer resilient layer and an inner mesh layer
      a pair of end panels each having a waterproof outer resilient layer and an inner mesh layer;
      a bottom panel; and,
      a top panel;
   wherein said collapsible frame is transformable therebetween an extended state and a collapsed state;
   wherein said tanning enclosure provides a privacy means and a protection means therefor an occupant;
   wherein said tanning enclosure provides a collapsible and transportable means;
   wherein said first side panel, said second side panel, said pair of end panels, said bottom panel, and said top panel are coplanar when detached from said collapsible frame;
   wherein said top panel is registered parallel to said bottom panel when folded to a closed position and engaged with said second side panel;
   wherein said mesh layer is accessed by rolling up said outer layer and upwardly securing it with an integral fastener to said collapsible frame of each of said first side panel, said second side panel, and said pair of end panels;
   wherein said top panel is hingedly connected to an entire longitudinal length of a top edge of said first side panel via a connection material.

2. The tanning enclosure of claim 1, wherein said collapsible frame is fabricated of lightweight tubing.

3. The tanning enclosure of claim 2, wherein said collapsible frame further comprises four "U"-shaped connection pieces, four end pieces, and two longitudinal pieces;
   wherein a pair of four end pieces interconnect with a pair of said four "U"-shaped connection pieces to produce an end frame element;
   wherein said two longitudinal pieces interconnect a pair of end frame elements to produce said extended state;
   wherein said collapsible frame provide a supporting means thereto said cover enclosure when is said extended state.

4. The tanning enclosure of claim 3, wherein each of said four end pieces, and said two longitudinal pieces each comprise a tapered end to interconnect with a connection aperture.

5. The tanning enclosure of claim 4, further comprising an attachment means for removably attaching said first side panel, said second side panel, said pair of end panels, said bottom panel, and said top panel thereto said collapsible frame therein said extended state.

6. The tanning enclosure of claim 1, wherein said pair of end panels each comprise an entrance and exit aperture with a securing means which permits access for said occupant to an interior space when said collapsible frame is in said extended state.

7. The tanning enclosure of claim 6, further comprising at least one storage pocket secured therewith a fastening means integrally disposed thereon an inner surface thereof said first side panel, said second side panel, and said pair of end panels.

8. The tanning enclosure of claim 1, wherein said top panel comprises a material that filters sunlight passing through.

9. The tanning enclosure of claim 1, further comprising a storage enclosure further comprising a handle thereon an exterior thereof.

10. A tanning enclosure, comprising:
    a collapsible frame, comprising a plurality of interconnected resilient tubular pieces;
    a cover enclosure removably attachable thereto said collapsible frame, further comprising
       a first side panel having a waterproof outer resilient layer and an inner mesh layer;
       a second side panel having a waterproof outer resilient layer and an inner mesh layer
       a pair of end panels each having a waterproof outer resilient layer and an inner mesh layer;
       a bottom panel; and,
       a top panel; and,
    a storage enclosure, comprising a handle thereon an exterior thereof;
    wherein said collapsible frame is transformable therebetween an extended state and a collapsed state;
    wherein said tanning enclosure provides a privacy means and a protection means therefor an occupant;
    wherein said tanning enclosure provides a collapsible and transportable means;
    wherein said first side panel, said second side panel, said pair of end panels, said bottom panel, and said top panel are coplanar when detached from said collapsible frame;
    wherein said top panel is registered parallel to said bottom panel when folded to a closed position and engaged with said second side panel;
    wherein said mesh layer is accessed by rolling up said outer layer and upwardly securing it with an integral fastener to said collapsible frame of each of said first side panel, said second side panel, and said pair of end panels;
    wherein said top panel is hingedly connected to an entire longitudinal length of a top edge of said first side panel via a connection material; and,
    wherein said storage enclosure provides a storage means for retaining said collapsed state thereof said collapsible frame and said cover enclosure therein.

11. The tanning enclosure of claim 10, wherein said collapsible frame further comprises four "U"-shaped connection pieces, four end pieces, and two longitudinal pieces;
    wherein a pair of four end pieces interconnect with a pair of said four "U"-shaped connection pieces to produce an end frame element;
    wherein said two longitudinal pieces interconnect a pair of end frame elements to produce said extended state;
    wherein said collapsible frame provide a supporting means thereto said cover enclosure when is said extended state.

12. The tanning enclosure of claim 11, wherein each of said four end pieces, and said two longitudinal pieces each comprise a tapered end to interconnect with a connection aperture of said four "U"-shaped connection pieces.

13. The tanning enclosure of claim 12, further comprising an attachment means for removably attaching said first side panel, said second side panel, said pair of end panels, said bottom panel, and said top panel thereto said collapsible frame therein said extended state.

14. The tanning enclosure of claim 10, wherein said pair of end panels each comprise an entrance and exit aperture with a securing means which permits access for said occupant to an interior space when said collapsible frame is in said extended state.

15. The tanning enclosure of claim 14, further comprising at least one (1) storage pocket secured therewith a fastening means integrally disposed thereon an inner surface thereof said first side panel, said second side panel, and said pair of end panels.

16. The tanning enclosure of claim 15, wherein said top panel comprises a material that filters sunlight passing through.

* * * * *